US007212609B2

(12) United States Patent
Nagamine et al.

(10) Patent No.: US 7,212,609 B2
(45) Date of Patent: May 1, 2007

(54) PATIENT POSITIONING DEVICE AND PATIENT POSITIONING METHOD

(75) Inventors: Yoshihiko Nagamine, Hitachi (JP); Shinichiro Fujitaka, Hitachi (JP); Takurou Honda, Mito (JP); Hiroshi Akiyama, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/432,363

(22) Filed: May 12, 2006

(65) Prior Publication Data

US 2006/0203958 A1    Sep. 14, 2006

Related U.S. Application Data

(63) Continuation of application No. 10/767,330, filed on Jan. 30, 2004.

(30) Foreign Application Priority Data

Mar. 5, 2003 (JP) .............................. 2003-058199

(51) Int. Cl.
   *A61N 5/10* (2006.01)
   *A61B 6/04* (2006.01)
(52) U.S. Cl. ........................... 378/65; 378/95; 378/205
(58) Field of Classification Search .................. 378/65, 378/95, 205
   See application file for complete search history.

(56) References Cited

U.S. PATENT DOCUMENTS

| | | | |
|---|---|---|---|
| 4,907,252 A | 3/1990 | Aichinger et al. | |
| 5,039,867 A | 8/1991 | Nishihara et al. | |
| 5,207,223 A * | 5/1993 | Adler | 600/427 |
| 5,825,845 A * | 10/1998 | Blair et al. | 378/62 |
| 6,307,914 B1 * | 10/2001 | Kunieda et al. | 378/65 |
| 6,322,249 B1 | 11/2001 | Wofford et al. | |
| 6,560,354 B1 | 5/2003 | Maurer et al. | |
| 2002/0188194 A1 | 12/2002 | Cosman | |

FOREIGN PATENT DOCUMENTS

DE    34 36 444 A    4/1986

(Continued)

*Primary Examiner*—Edward J. Glick
*Assistant Examiner*—Thomas R. Artman
(74) *Attorney, Agent, or Firm*—Dickstein Shapiro LLP

(57) ABSTRACT

The invention is intended to always ensure a sufficient level of patient positioning accuracy regardless of the skills of individual operators. In a patient positioning device for positioning a patient couch 59 and irradiating an ion beam toward a tumor in the body of a patient 8 from a particle beam irradiation section 4, the patient positioning device comprises an X-ray emission device 26 for emitting an X-ray along a beam line m from the particle beam irradiation section 4, an X-ray image capturing device 29 for receiving the X-ray and processing an X-ray image, a display unit 39B for displaying a current image of the tumor in accordance with a processed image signal, a display unit 39A for displaying a reference X-ray image of the tumor which is prepared in advance, and a positioning data generator 37 for executing pattern matching between a comparison area A being a part of the reference X-ray image and including an isocenter and a comparison area B or a final comparison area B in the current image, thereby producing data used for positioning of the patient couch 59 during irradiation.

12 Claims, 11 Drawing Sheets

FOREIGN PATENT DOCUMENTS

| | | |
|---|---|---|
| JP | 05-021506 | 1/1993 |
| JP | 07-198336 | 8/1995 |
| JP | 08-084740 | 4/1996 |
| JP | 11-019234 | 1/1999 |
| JP | 2000-510023 | 8/2000 |
| JP | 2001-161839 | 6/2001 |
| JP | 2002-126106 | 5/2002 |
| WO | WO 98 18523 A | 5/1998 |

* cited by examiner

PATIENT POSITIONING DEVICE AND PATIENT POSITIONING METHOD

CROSS-REFERENCE TO RELATED APPLICATIONS

This application is a continuation of U.S. patent application Ser. No. 10/767,330, filed Jan. 30, 2004, which claims priority under 35 USC 119 to Japanese Application No. 2003-058199, dated Mar. 5, 2003, which are incorporated herein by reference.

BACKGROUND OF THE INVENTION

1. Field of the Invention

The present invention relates to a patient positioning device and a patient positioning method. More particularly, the present invention relates to a patient positioning device and a patient positioning method, which are suitably employed in a particle beam treatment system for irradiating a charged particle beam (ion beam), such as a proton and a carbon ion, to a tumor for treatment.

2. Description of the Related Art

There is known a treatment method of setting an isocenter (irradiation target center) at a tumor, e.g., a cancer, in the body of a patient and irradiating an ion beam, such as a proton, to the tumor. An apparatus for use with such a treatment method comprises a charged particle beam generator, a beam transport system, and a rotating gantry. An ion beam accelerated by the charged particle beam generator reaches the rotating gantry through a first beam transport system, and is irradiated to the tumor from an irradiation nozzle after having passed through a second beam transport system provided in the rotating gantry.

In the apparatus thus constructed, the patient must be caused to lie in a proper position relative to the irradiation nozzle so that the ion beam is irradiated to only the isocenter without damaging normal cells. A patient positioning device for use with irradiation of the particle beam is a device for positioning a patient couch to make the patient lie in the proper position (see, e.g., Patent Reference 1, JP,A 2000-510023 (pages 27–31 and FIGS. 1, 6, 7A and 7B)). Particularly, in the case of irradiating an ion beam, for example, a proton beam, activation energy for the proton beam is selected so as to stop protons at the isocenter and apply most of the proton energy to only cells in the tumor, which is positioned at the isocenter, by utilizing a characteristic that most of the proton energy is released upon the stop of protons (this phenomenon is called "Brag peak"). Therefore, the alignment of the ion beam with the isocenter is very important.

In a known patient positioning device, to ensure accurate positioning of the patient relative to the irradiation nozzle, the position of the isocenter is decided beforehand relative to monuments (or landmarks, i.e., anatomical base points; for example, portions of the patient's skeleton), which are set in the patient body. Usually, the position of the isocenter including a diseased tissue, e.g., a tumor, is marked on a DRR (digitally reconstructed radiograph). Then, display images looking from other directions are edited as required.

In a state where the patient lies on a patient couch prior to the irradiation of a proton beam, an X-ray source is disposed on a path of the proton beam, and an X-ray receiver is disposed on the side opposed to the X-ray source with respect to the patient along the path of the proton beam. The X-ray receiver produces an X-ray image of the tumor and its surroundings in the patient body. On this occasion, in order to align the isocenter on a beam line, through which the proton beam passes in the irradiation nozzle, with the tumor, the direction in and the distance by which the patient couch is moved relative to the irradiation nozzle must be determined by employing the offset distance on an X-ray image from each of the particular monuments to the center of the X-ray beam and the offset distance on the DRR from the same particular monument to the isocenter. Positioning control of the patient couch is performed based on the thus-determined direction and distance of movement of the patient couch.

SUMMARY OF THE INVENTION

In the prior art described above, an operator, e.g., a doctor, designates plural monument positions on the skeleton of the patient on a DRR as a reference image, displayed on a display unit, and also designates the same positions of the same plural monuments on a captured image as an X-ray image obtained by the X-ray receiver, displayed on the display unit. In spite of the operator having intended to designate the same positions of the same plural monuments on both the screen images, therefore, there is a fear that the respective corresponding positions designated on the DRR and the captured image are not in alignment and offset from each other. If the respective designated positions to be kept in alignment on the DRR and the captured image are offset from each other, deterioration of accuracy occurs in aligning the patient couch (particularly the tumor), which should be properly positioned based on both the designated positions, with the beam line.

Accordingly, it is an object of the present invention to provide a patient positioning device and a patient positioning method, which can increase the accuracy in positioning of a patient.

To achieve the above object, the present invention is featured in that a processing unit executes pattern matching between a part of first image information in a first set area including an isocenter, the first image information representing a tumor in the body of the patient and serving as a reference including the isocenter, and a part of second image information in a second set area including a position corresponding to a path of a charged particle beam, the second image information representing a portion of the patient lying across the path of the charged particle beam, thereby producing information used for positioning of the patient (couch). Since the positioning information is produced through the pattern matching between the first image information in the first set area and the second image information in the second set area, accuracy in producing the positioning information is avoided from being affected by the skill of an operator, such as required when designating the positions of monuments, unlike the case of producing the positioning information based on the positions of monuments designated by the operator. As a result, the positioning accuracy can be increased regardless of the skills of individual operators.

DESCRIPTION OF THE PREFERRED EMBODIMENTS

One embodiment of the present invention will be described below with reference to the drawings.

Figure 1:
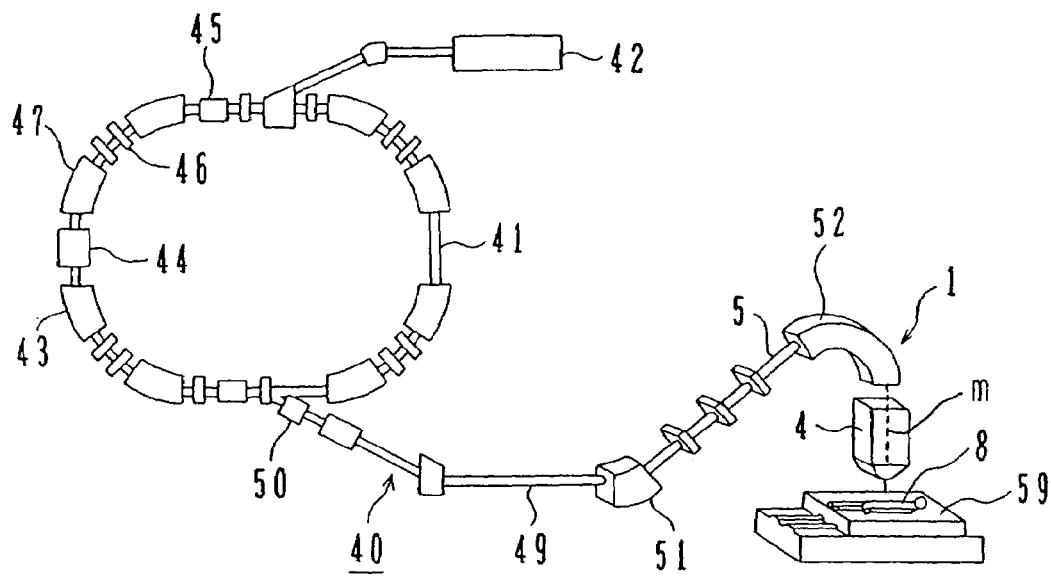
FIG. 1 is an overall view showing a construction of a medical particle beam irradiation system to which a patient positioning device according to one preferred embodiment of the present invention is applied.
Figure 2:
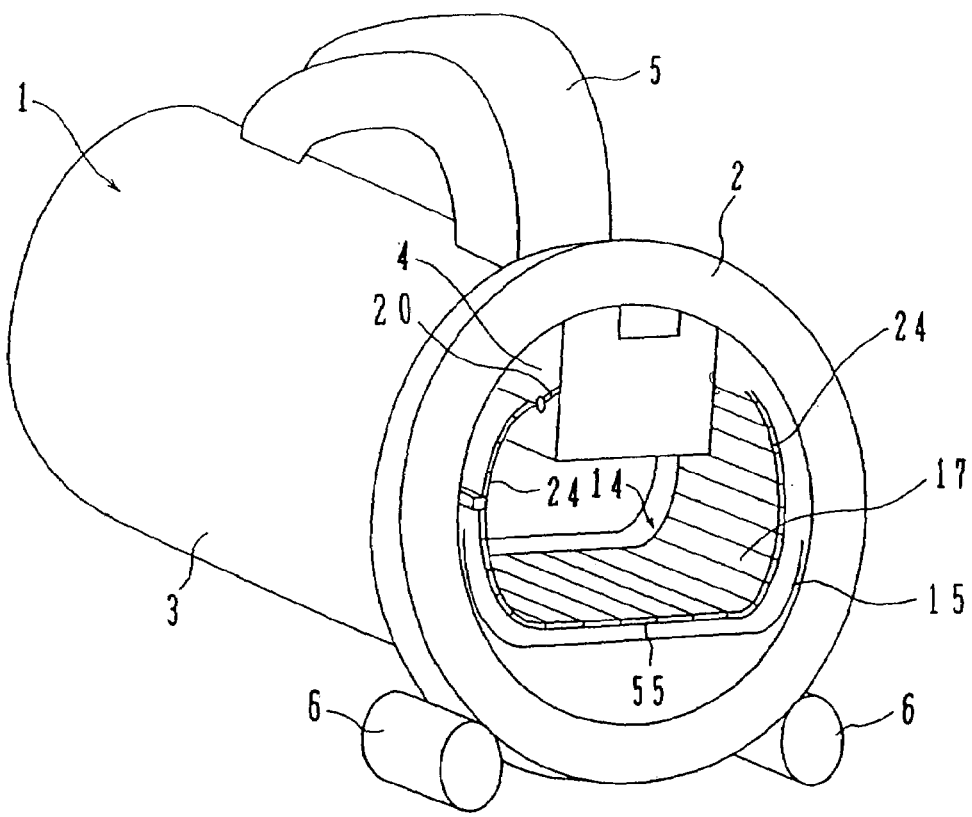
FIG. 2 is a perspective view of a rotating gantry shown in FIG. 1.

With reference to FIGS. 1 and 2, a description is first made of a medical particle beam irradiation system to which a patient positioning device of this embodiment is applied.

A medical particle beam irradiation system 40 comprises a charged particle beam generator 41 and a rotating gantry 1. The charged particle beam generator (also called a particle beam generator) 41, an ion source (not shown), a pre-stage accelerator 42, and a synchrotron 43. Ions (e.g., proton ions or carbon ions) generated from the ion source are accelerated by the pre-stage accelerator (e.g., a linear accelerator) 42. An ion beam (proton beam) accelerated by the pre-stage accelerator 42 enters the synchrotron 43. In this embodiment, a proton beam is employed as the ion beam. The ion beam in the form of a charged particle beam (also called a particle beam) is accelerated by being given with energy applied as high-frequency electric power from a high-frequency accelerator cavity 44 in the synchrotron 43. After the energy of the ion beam circling in the synchrotron 43 has been increased up to a preset level of energy (usually 100 to 200 MeV), a high frequency wave is applied to the ion beam from a high-frequency applying device 45 for exiting of the ion beam. With the application of that high frequency wave, the ion beam circling within a stable limit high frequency wave is caused to shift out of the stable limit and to exit from the synchrotron 43 through an exit deflector 50. Upon the exiting of the ion beam, currents supplied to electromagnets, i.e., quadrupole electromagnets 46 and deflection electromagnets 47, disposed in the synchrotron 43 are held at respective setting values and the stable limit is also held substantially constant. By stopping the application of high-frequency electric power to the high-frequency applying device 45, the exiting of the ion beam from the synchrotron 43 is stopped.

The ion beam having exited from the synchrotron 43 reaches, through a beam transport system 49, a particle beam irradiation section (also called a particle beam irradiator) 4 for irradiating the ion beam. The ion beam is irradiated from the particle beam irradiation section 4 to a tumor (cancer) in the body of a patient 8 lying on a treatment couch (patient couch) 59. The particle beam irradiation section 4 generates the ion beam providing a dose distribution optimum for the treatment utilizing the particle beam.

Figure 3:
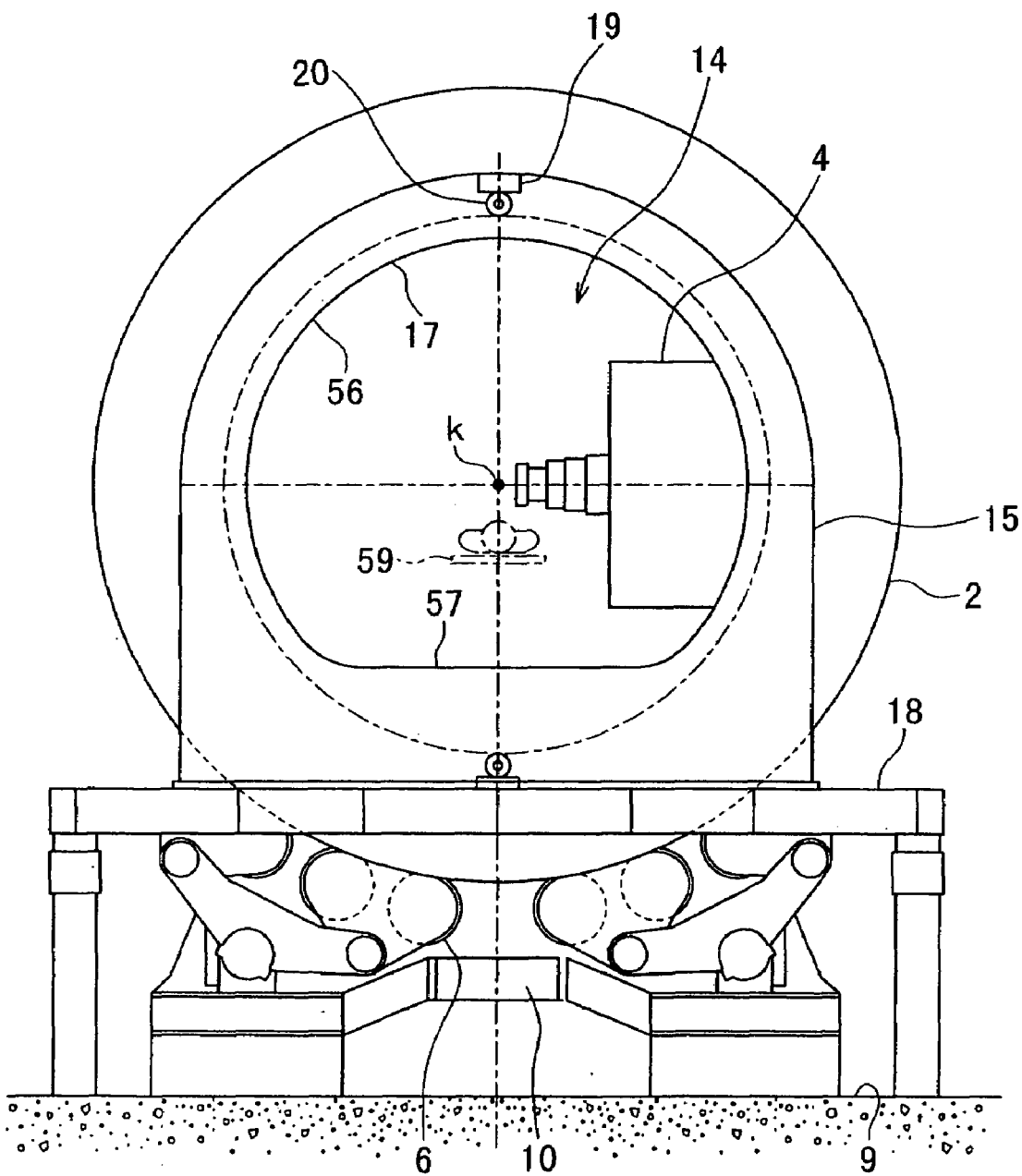
FIG. 3 is a front view of the rotating gantry shown in FIG. 1.

The rotating gantry 1 comprises a substantially cylindrical rotating drum (rotating body) 3 having a front ring 2, and a motor (rotating device), not shown, for rotating the rotating drum 3. The front ring 2 provided at one end of the rotating drum 3 is supported by a plurality of rotatable support rolls 6. As shown in FIG. 3, the support rolls 6 are rotatably mounted to a support unit 10 installed on a rotating gantry installation area (building base) 9. Though not shown, the other ring (having an outer diameter equal to that of the front ring 2) provided at the other end of the rotating drum 3 is similarly supported by a plurality of support rolls 6 which are rotatably mounted to the other support unit 10. An inverted U-shaped beam transport system 5 serving as a part of the beam transport system 49 and the particle beam irradiation section 4 are mounted on the rotating drum 3 and are rotated with the rotation of the rotating gantry 1. The beam transport system 5 includes electromagnets, such as deflecting electromagnets 51, 52. A treatment gauge (treatment chamber) 14 is formed inside the rotating drum 3.

Figure 4:
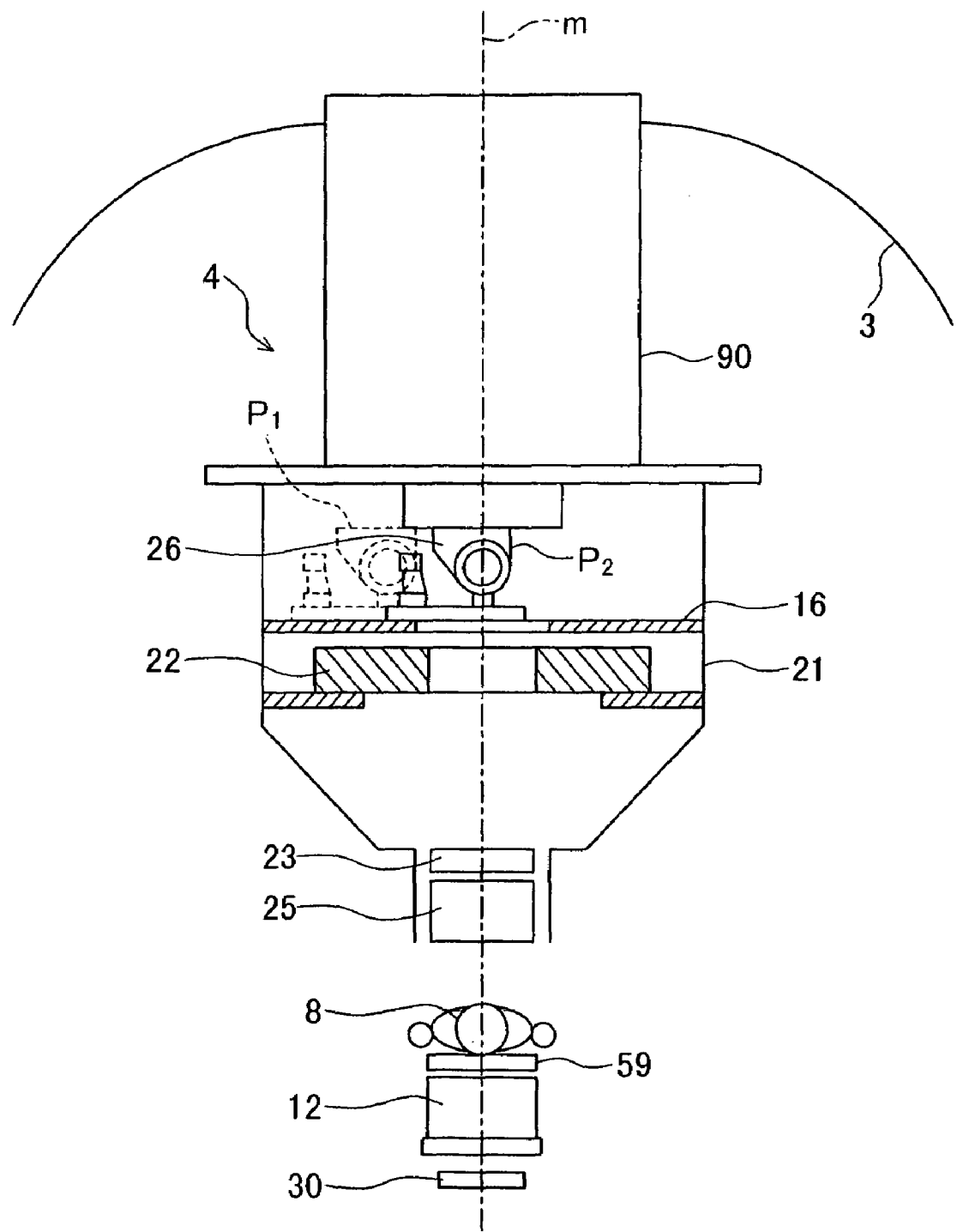
FIG. 4 is a schematic view showing a vertical sectional structure of a particle beam irradiation section shown in FIG. 1.

FIG. 4 is a schematic view showing a vertical sectional structure of the particle beam irradiation section 4. In FIG. 4, the particle beam irradiation section 4 comprises a casing 90 mounted to the rotating drum 3 and coupled to the inverted U-shaped beam transport system 5, and a snout 21 provided at one end of the casing 90, i.e., on the side nearer to the nozzle end. Inside the casing 90 and the snout 21, a scatterer (not shown), a ring collimator 22, a patient collimator 23, and a bolus 25 are disposed, by way of example, in this order from the upstream side in the direction of advance of the ion beam introduced from the beam transport system 5. Those components are successively arranged to lie on a beam line m along which the ion beam passes. Additional units, such as an SOBP forming unit of ridge filter type and a range adjusting unit having a pair of wedge-shaped blocks, may also be disposed to lie on the beam line m.

The ring collimator 22 is to roughly collimate an irradiation field of the ion beam and is mounted to the snout 21 through a mounting member (not shown). The patient collimator 23 is to shape the ion beam in match with the tumor shape in the direction perpendicular to the beam line m, and it is also mounted to the snout 21 through a mounting member (not shown).

The ion beam formed by the particle beam irradiation section 4 of the above-described construction and having the proper irradiation field releases its energy in the tumor in the body of the patient 8, thereby forming a high-dose area.

Incidentally, an X-ray emission device (X-ray tube) 26 serving as an X-ray source will be described later.

Returning to FIGS. 2 and 3, the medical particle beam irradiation system 40 includes an irradiation chamber 55 for the particle beam treatment in the rotating drum 3 of the rotating gantry 1. The irradiation chamber 55 for the particle beam treatment is provided with a fixed annular frame (ring member) 15. The annular frame 15 is disposed on one end side of the rotating drum 3, i.e., on the same side as the front ring 2, and is fixed to a mount base 18 installed in the rotating gantry installation area 9. In addition, the other annular frame (not shown) is disposed on the other end side of the rotating drum 3 so as to sandwich a path of movement of the particle beam irradiation section 4 between itself and the annular frame 15. The other annular frame is supported by a plurality of support rolls 20 which are rotatably held by a support frame 19 fixed to an inner surface of the rotating drum 3. In other words, the other annular frame is rotatable relative to the rotating drum 3 through the support rolls 20. These annular frames including the one 15 have guide grooves (not shown) each comprising a lower horizontal portion and an upper arc-shaped portion, which are formed in respective side surfaces of the annular frames in an opposed relation to each other. Each of the guide grooves has a substantially semi-cylindrical shape defined by the lower horizontal portion and the upper arc-shaped portion.

The irradiation chamber 55 for the particle beam treatment is further provided with a movable floor 17. The movable floor 17 has a freely bendable articulated structure such that it comprises a number of plates 24 and every adjacent two of the plates 24 are coupled to each other by links (not shown). One end of the movable floor 17 is engaged in the guide groove of the annular frame 15, and the other end of the movable floor 17 is engaged in the guide groove of the other annular frame. Further, circumferential opposite ends of the movable floor 17 are connected to the particle beam irradiation section 4. When the motor is driven to rotate the rotating gantry 1, the particle beam irradiation section 4 is also rotated in the same rotating direction as the rotating gantry 1. Correspondingly, the movable floor 17 connected to the particle beam irradiation section 4 is pulled together and moved in the same rotating direction. The movement of the movable floor 17 is smoothly performed along the guide grooves of the annular frames including the one 15. The movable floor 17 is made up of a horizontal floor portion 57 formed by the horizontal portions of the guide grooves in the lower side of the annular frames including the one 15, and an arc-shaped wall portion 58 formed by the arc-shaped portions of the guide grooves in the upper side of the annular frames including the one 15. The treatment gauge 14 is formed within the movable floor 17. The treatment couch 59 is inserted in the treatment gauge 14 when the ion beam is irradiated to the patient from the particle beam irradiation section 4.

Figure 5:
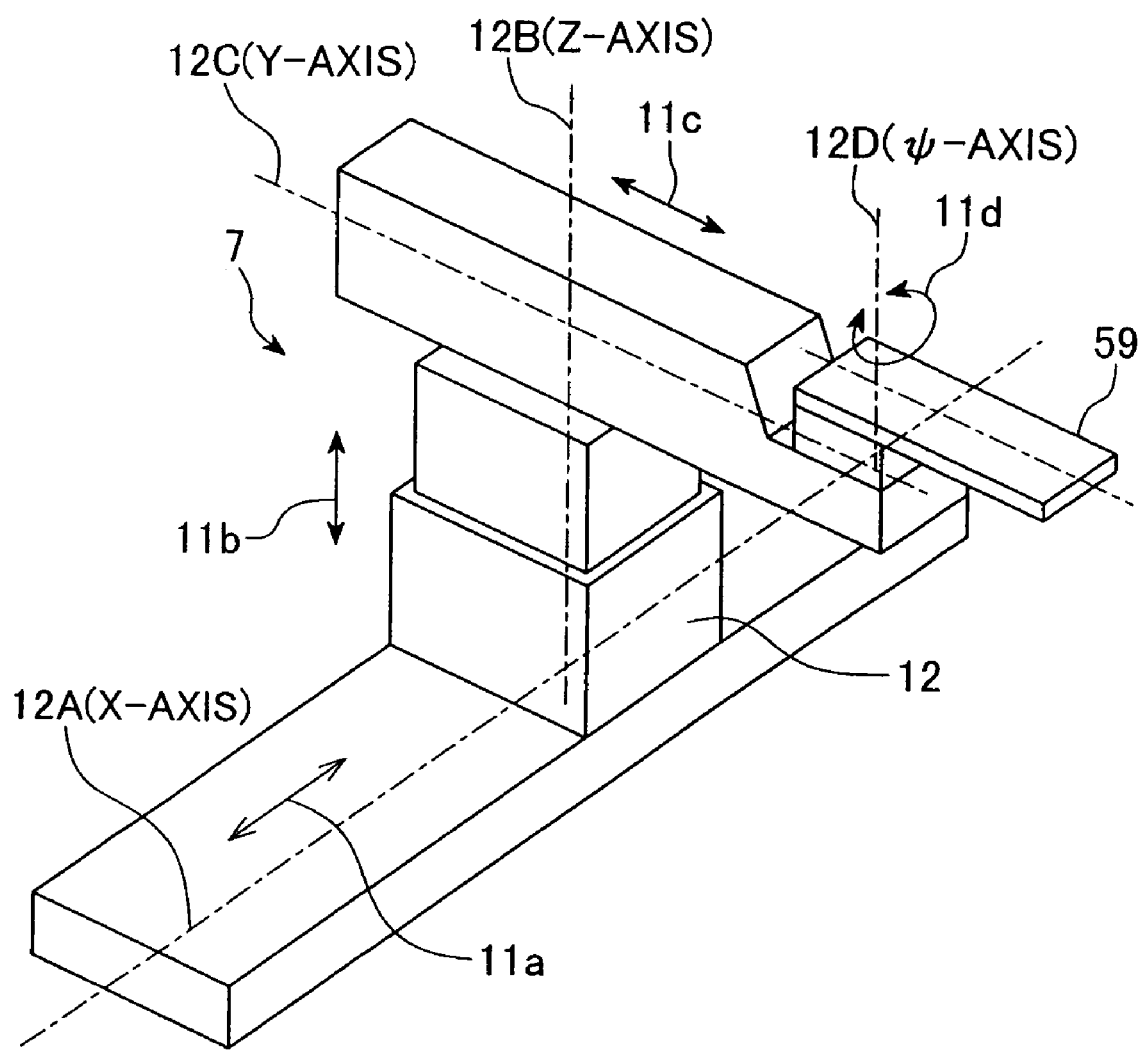
FIG. 5 is a conceptual view showing detailed functions of a couch driver for driving a patient couch shown in FIG. 1.

As shown in FIG. 5, a treatment bench 7 comprises a couch driver 12 and the treatment couch 59 installed on the couch driver 12. The treatment bench 7 is installed outside the rotating gantry 1 in an opposed relation to the front ring 2 within a treatment couch installation area (not shown) located at a level elevated one step from the rotating gantry installation area 9 (see FIG. 3). As seen from a conceptual view of FIG. 5, the couch driver 12 has four articulation axes 12A, 12B, 12C and 12D, and includes motors 11*a*, 11*b*, 11*c* and 11*d* for driving the treatment couch 59. Driving of the motor 11*a* moves the treatment couch 59 in the direction of the articulation axis 12A (X-axis) that is horizontally extended parallel to the front ring 2. Driving of the motor 11*b* moves the treatment couch 59 in the direction of the articulation axis 12B (Z-axis) that is perpendicular to the articulation axis 12A. Driving of the motor 11*c* moves the treatment couch 59 in the direction of the articulation axis 12C (Y-axis) that is perpendicular to both the articulation axis 12A (X-axis) and the articulation axis 12B (Z-axis) and is extended in the direction of a rotation axis of the rotating gantry 1. Thus, the treatment couch 59 is moved into and out of the treatment gauge 14 with the driving of the motor 11*c*. Furthermore, driving of the motor 11*d* rotates the treatment couch 59 about the articulation axis 12D ($\psi$-axis) that is perpendicular to the articulation axis 12C (Y-axis).

The patient positioning device of this embodiment is provided in the medical particle beam irradiation system 40 having the basic construction described above. The construction and functions of the patient positioning device will be described in detail below.

Figure 6:
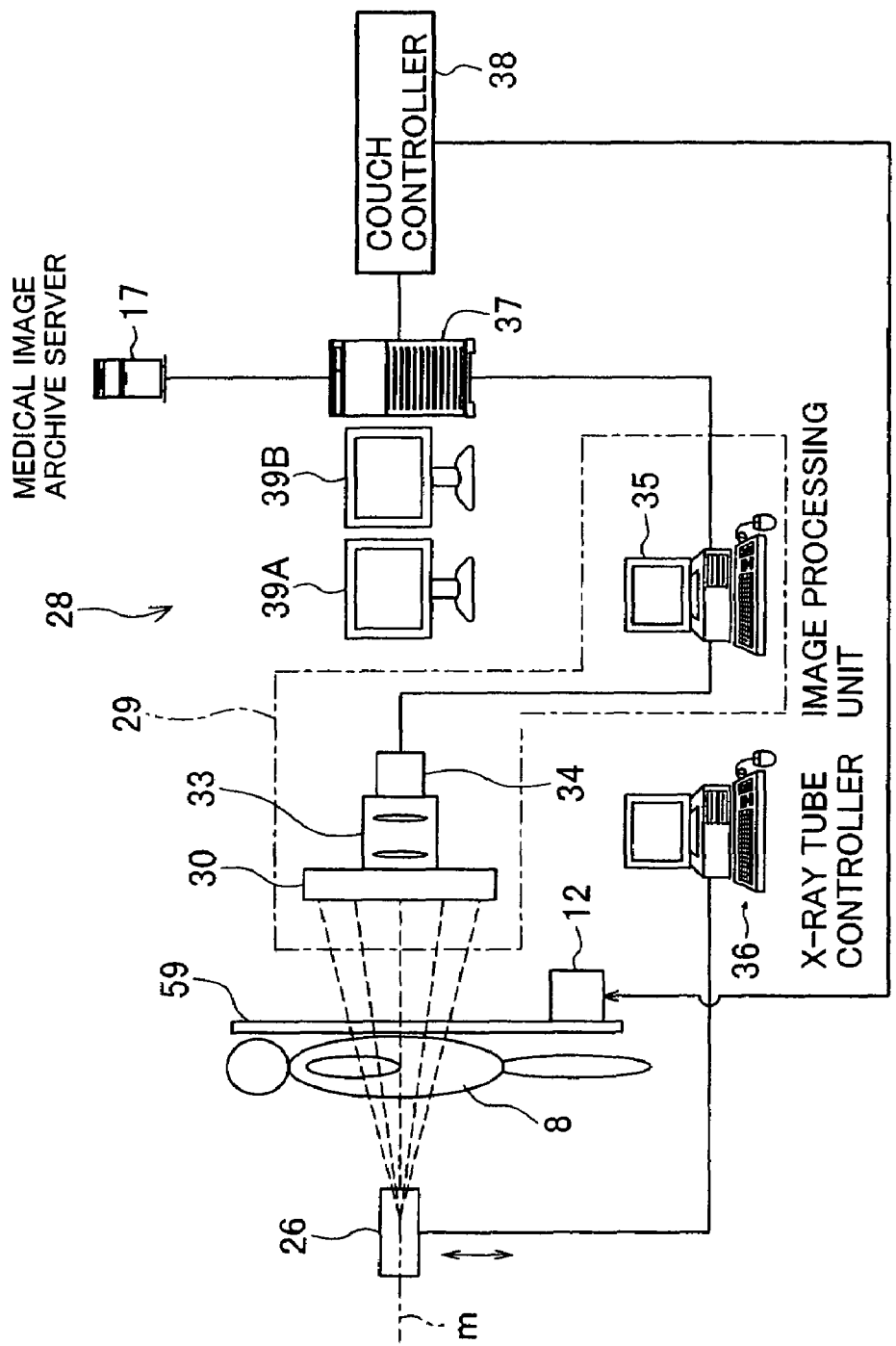
FIG. 6 is a schematic view showing a construction of the patient positioning device according to the one preferred embodiment of the present invention.

As shown in FIG. 6, a patient positioning device 28 comprises an X-ray emission device (X-ray tube or source) 26, an X-ray image capturing device (image information generator) 29, an X-ray tube controller 36, a positioning data generator (positioning information generator) 37 having not-shown input means (such as a keyboard and a mouse), a medical image archive server 17, a couch controller 38, and display units 39A, 39B. The positioning data generator 37 is constituted a work station (processing unit).

Figure 7:
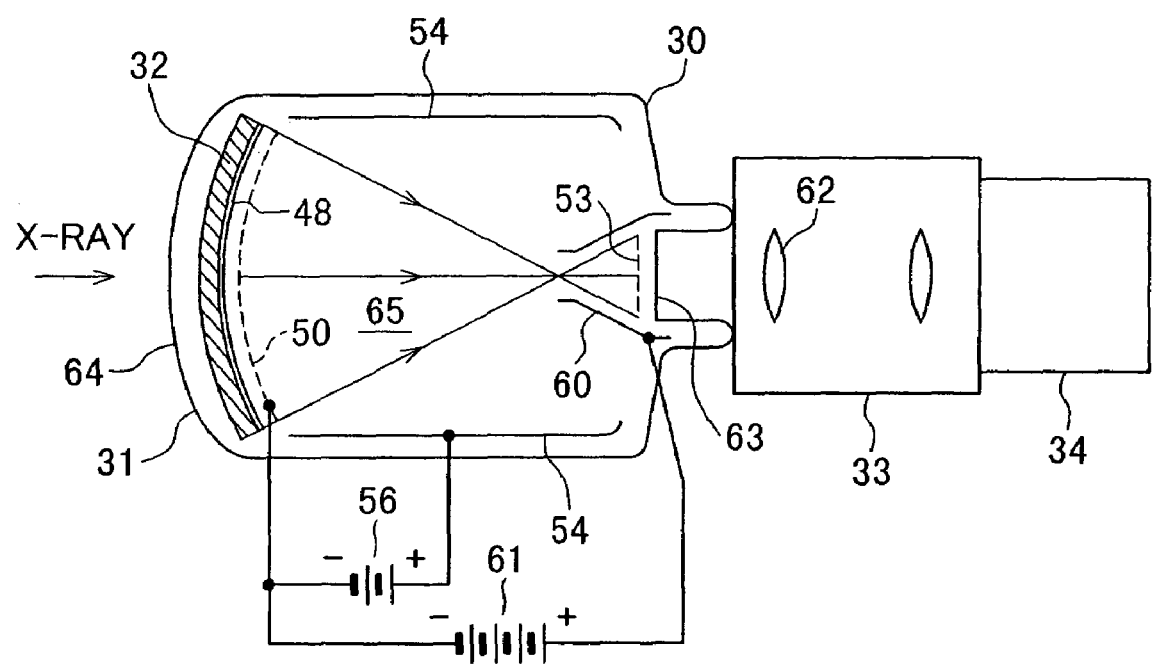
FIG. 7 is a detailed sectional view showing a structure of an X-ray fluorescence multiplier shown in FIG. 6.

The X-ray image capturing device 29 comprises an X-ray fluorescence multiplier (X-ray image intensifier) 30, an optical system 33, and a CCD camera (image information producing unit) 34. Inside a vacuum vessel 31, as shown in FIG. 7, a fluorescence film board 32 is disposed on the side nearer to an inlet window 64, and an output fluorescence film 53 is disposed on the side nearer to an outlet window 63. The fluorescence film board 32 has an input fluorescence film (X-ray entry device or X-ray transducer) 48 disposed on its rear side (i.e., on the side opposed to the inlet window 64). The output fluorescence film 53 has a smaller diameter than the input fluorescence film 48. A photocathode 50 is disposed in contact with the input fluorescence film 48. A converging electrode 54 is disposed in the vacuum vessel 31 so as to surround a photoelectron path 65. An anode 60 surrounding the output fluorescence film 53 is also disposed in the vacuum vessel 31. A voltage is applied between the photocathode 50 and the converging electrode 54 from a convergence power supply 56. Further, a voltage is applied between the photocathode 50 and the anode 60 from an anode power supply 61.

The X-ray image capturing device 29 is mounted to the rotating drum 3 of the rotating gantry 1 and is rotated together with the rotation of the rotating gantry 1. The X-ray image capturing device 29 is positioned on the beam line m on the side opposed to the particle beam irradiation section 4 with respect to the treatment couch 59.

As shown in FIG. 4, the X-ray emission device 26 is provided on a support member 16, which is mounted to the snout 21, to be movable in a direction perpendicular to the beam line m. The support member 16 has an opening through which the ion beam and the X-ray pass. Usually (other than the time for the positioning of the treatment couch 59, e.g., during the irradiation of the ion beam), the X-ray emission device 26 is retreated to a position $P_1$ away from the beam line m.

When the patient 8 lies down on the treatment couch 59 for starting the treatment with the irradiation of the ion beam, an operator, e.g., a doctor, inputs a command for movement of the treatment couch 59 to the couch controller 38 by using an input device (not shown) of the couch controller 38 so that a cross mark drawn on the body surface of the patient 8 (the cross mark being displayed by a laser so as to locate right above a tumor) is positioned on the beam line m. Thus, in accordance with the movement command, the couch controller 38 controls the couch driver 12 to move the treatment couch 59 so that the cross mark on the patient's body surface is aligned with the beam line m. With this alignment, an offset between the tumor and the beam line m is held within the range on the order of millimeter.

Further, the operator inputs a command for starting advance of the X-ray emission device 26 to an X-ray tube controller 36, e.g., a personal computer, through an input means (not shown). The X-ray tube controller 36 having received the start command outputs an X-ray tube movement signal to a not-shown driver (e.g., a motor) for the X-ray emission device 26. In response to the X-ray tube movement signal, the X-ray emission device 26 is advanced to a position $P_2$ on the beam line m. Then, when the operator inputs a command for starting the irradiation of an X-ray to the X-ray tube controller 36, an X-ray irradiation start signal outputted from the X-ray tube controller 36 is inputted to the X-ray emission device 26. Correspondingly, the X-ray emission device 26 irradiates an X-ray beam toward the patient 8 along the beam line m.

The X-ray having penetrated the patient 8 is inputted to the vacuum vessel 31 through the inlet window 64 and then reaches the input fluorescence film 48 through the fluorescence film board 32 for conversion into a visible image. Light of the visible image is converted into photoelectrons by the photocathode 50. The photoelectrons are converged by the converging electrode 54 and then reach the output fluorescence film 53 through the anode 60 along the photoelectron path 65 for conversion into a bright visible image. This bright visible image is captured by the CCD camera 34 through lenses 62 in the optical system 33. The image captured by the CCD camera 34 is inputted to a personal computer (image processing unit) 35 serving as a first processing unit. The image processing unit 35 executes predetermined processing on the input image for the purpose of image processing (such as color correction and blur correction). Image data (also called current image data or captured image data), including a tumor image, which has been subjected to the image processing, is inputted to the positioning data generator 37 from the image processing unit 35.

Figure 8:
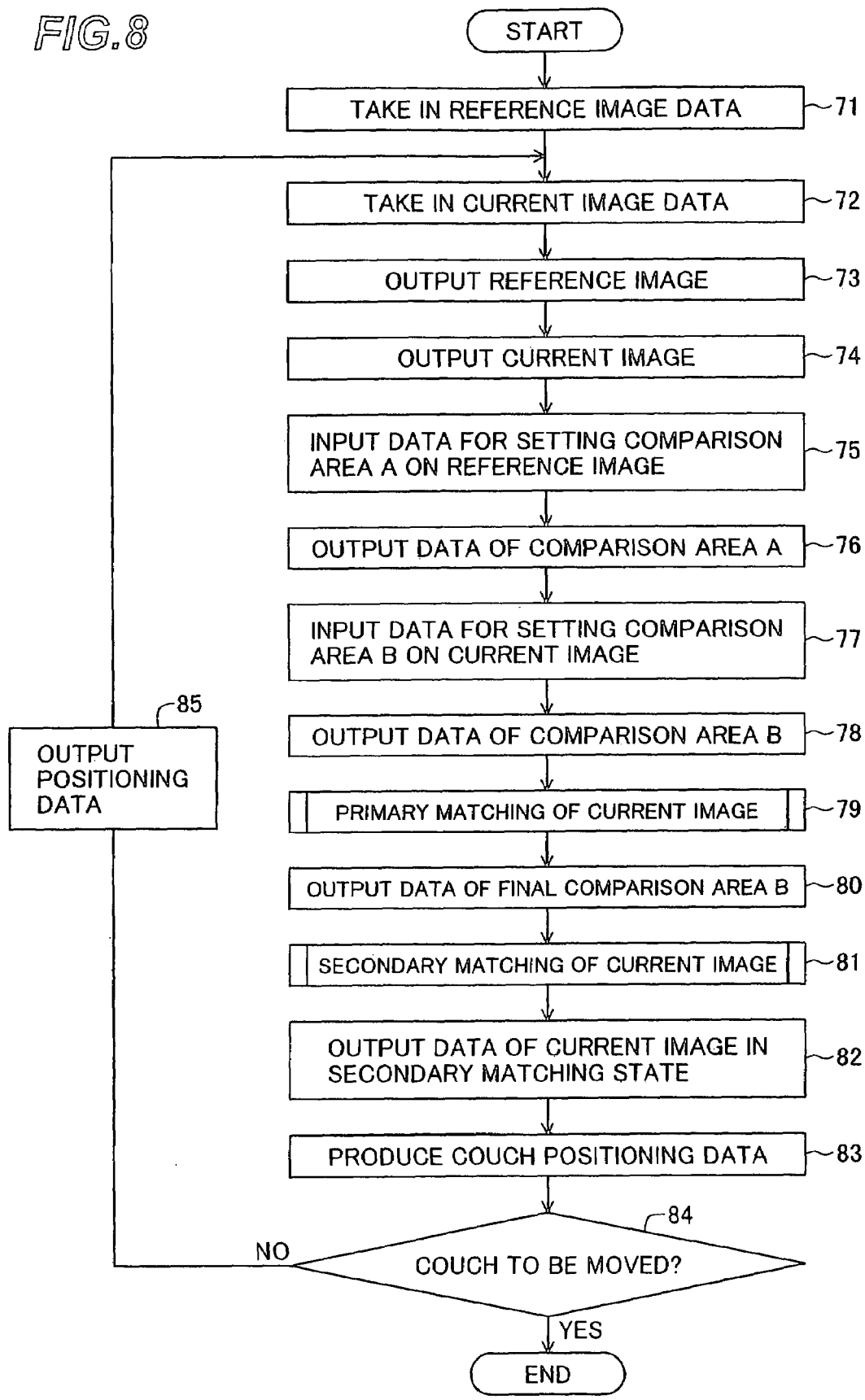
FIG. 8 is a flowchart showing a processing sequence executed by a positioning data generator shown in FIG. 6.

The positioning data generator 37 produces positioning data for the treatment couch 59 based on the current image data outputted from the X-ray image capturing device 29 and image data stored in the medical image archive server 17, and then outputs the produced positioning data to the couch controller 38. A sequence of processing executed by the positioning data generator 37 to produce the positioning data will be described below with reference to FIG. 8. This processing sequence is stored, as a program, in a memory (e.g., a not-shown ROM or other storage medium) provided in the positioning data generator 37.

The medical image archive server 17 accumulates and stores, as reference image data (control image data) serving as a positioning reference, data of a tomographic image of the relevant patient 8 captured by X-ray CT (e.g., a DRR image, or an X-ray image captured by the patient positioning device shown in FIG. 6 in advance, for example, until the day before the treatment day, or an image obtained by editing such an image using the known method in match with the direction in which the ion beam is now to be irradiated). When aligning the tumor in the body of the patient 8 with the beam line m, the reference image data is first loaded into a memory (not shown) of the positioning data generator 37 from medical image archive server 17 (step 71). In the following description, the expression "data (or information) is inputted to the positioning data generator 37" means that "the data (or information) is stored in the above-mentioned memory in the positioning data generator 37".

Then, the current image data of the tumor, which is outputted from the image processing unit 35 after being subjected to the above-mentioned image processing, is also inputted to the positioning data generator 37 (step 72).

Figure 9A:
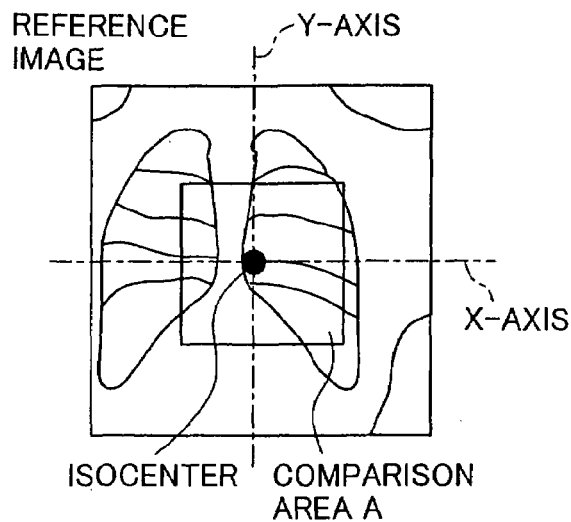
FIGS. 9(A), 9(B) and 9(C) show examples of screen images displayed on display units shown in FIG. 6.
Figure 9B:
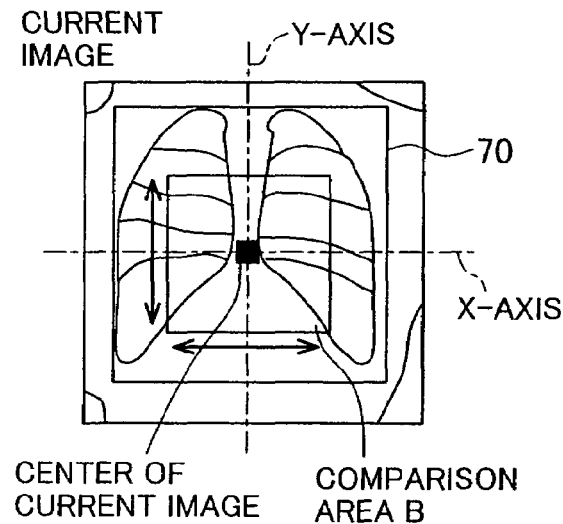

Subsequently, the reference image data taken into the positioning data generator 37 is outputted to the display unit (second display unit) 39A (step 73), and the current image data taken into the positioning data generator 37 is outputted to the display unit (first display units) 39B (step 74). With these steps, a reference image is displayed on the display unit 39A and a current image is displayed on the display unit 39B. FIG. 9(A) shows an example of a screen image of the reference image displayed on the display unit 39A, and FIG. 9(B) shows an example of a screen image of the current image displayed on the display unit 39B. At this time, the reference image displayed on the display unit 39A in step 73 does not yet indicate a frame of a comparison area A. Also, the current image displayed on the display unit 39B in step 74 does not yet indicate a frame of a comparison area B. The reference image and the current image may be displayed on one display unit side by side or in a superposed relation instead of separately displaying them on the respective display units 39A, 39B. As an alternative, the reference image and the current image may be displayed on a display of the image processing unit 35.

Thereafter, while looking at the reference image and the current image displayed on the display units 39A, 39B, the operator sets a predetermined comparison area (clipping area) A in the reference image displayed on the display unit 39A with the isocenter positioned at the center. The comparison area A (more exactly speaking, the frame of the comparison area A) is inputted for setting (clipping) by using the input unit of the positioning data generator 37. The comparison area A is employed as an area for comparison with the current image having the center aligned with the beam line m through pattern matching. The input data for setting the comparison area A is taken into the positioning data generator 37 (step 75). Then, display information of the set comparison area A (more exactly speaking, the frame of the set comparison area A), i.e., display information of the frame of the comparison area A, is outputted to the display unit 39A (step 76). As a result, the data of the frame of the comparison area A is displayed on the display unit 39A in a superposed relation to the reference image while the center of the comparison area A is aligned with the isocenter. FIG. 9(A) shows one practical example in which the data of the frame of the comparison area A is displayed on the reference image. A region inside the frame of the comparison area A defines the comparison area A. Instead of manually setting the comparison area A by the operator as described above, it is also possible to automatically set the comparison area A by the positioning data generator 37 (for example, through a step of automatically setting a preset area of a predetermined size with the isocener positioned at the center, or an area of a size variable depending on a treatment plan supplied from the medical image archive server 17).

Corresponding to the setting of the comparison area A, the positioning data generator 37 sets a comparison area B (more exactly speaking, a frame of the comparison area B), which has the same size as the comparison area A, on the current image displayed on the display unit 39B with the origin defined at the center (beam line m) of the current image (step 77). The setting of the size of the comparison area B is automatically performed using the setting input data that has been entered through the input unit of the positioning data generator 37 to set the comparison area A. The data of the comparison area B (more exactly speaking, the frame of the comparison area B) thus set is outputted to the display unit 39B (step 78). As a result, the data of the frame of the comparison area B is displayed on the display unit 39B in a superposed relation to the current image while the center of the comparison area B is aligned with the center of the current image. FIG. 9(B) shows one practical example in which the frame of the comparison area B is displayed on the current image. A region inside the frame of the comparison area B defines the comparison area B. Note that the comparison area B may be set with manual setting made by the operator.

Figure 10A:
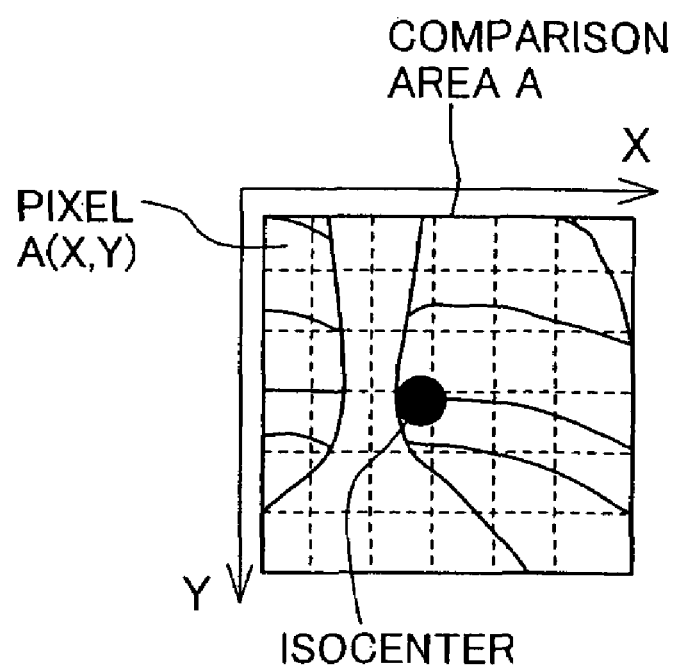
FIGS. 10(A) and 10(B) show other examples of screen images displayed on the display units shown in FIG. 6.
Figure 10B:
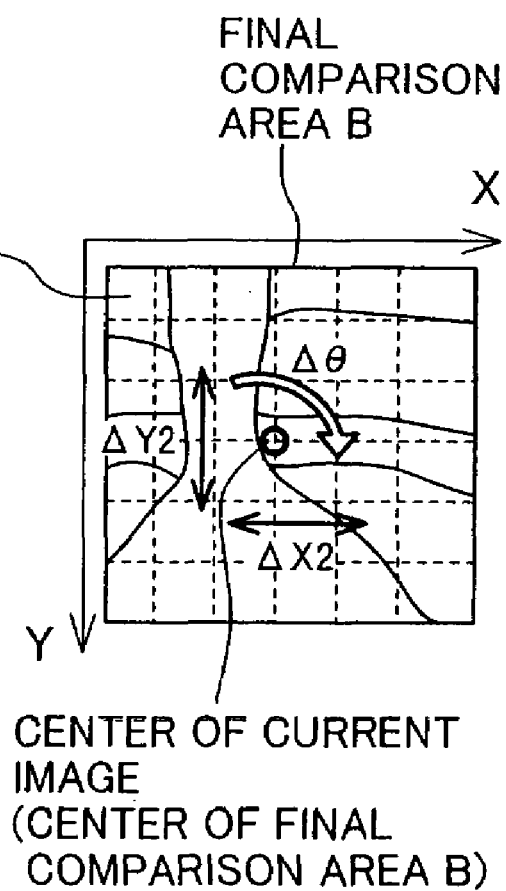
Figure 11:
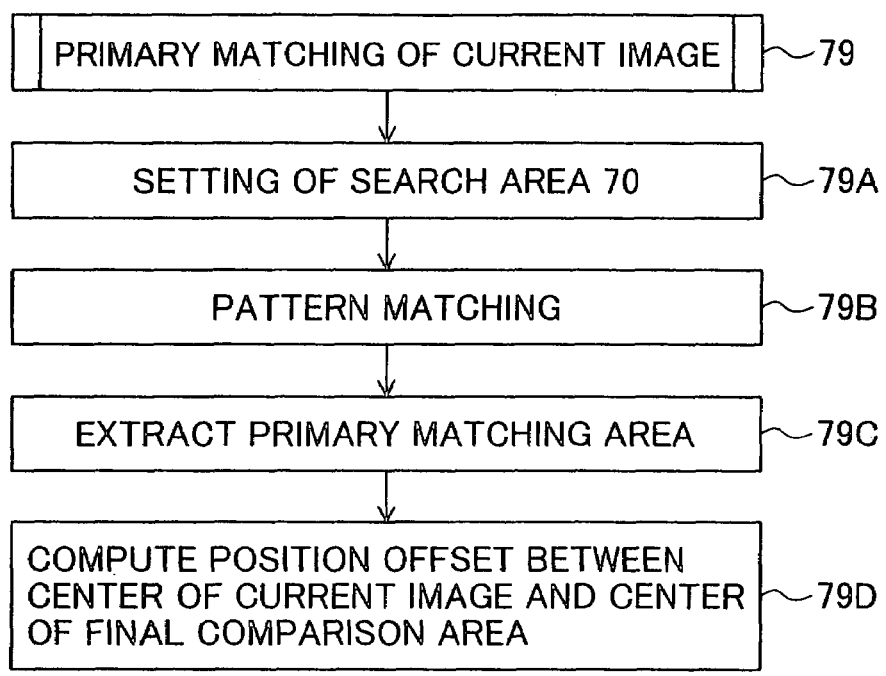
FIG. 11 is a flowchart showing a detailed processing sequence of step 79 shown in FIG. 8.

Then, the positioning data generator 37 executes primary pattern matching between the comparison area A and the comparison area B based on image similarity searching (e.g., pattern matching through comparison of pixel information) utilizing correlation between two images (step 79). The comparison area A and the comparison area B have the same number of pixels in each of the X- and Y-directions, and also have the same total number of pixels in the respective entire areas. Detailed processing of step 79 will be described below with reference to FIG. 11. First, a search area 70 (see FIG. 9(B)) is set which is smaller than the current image, but larger than the comparison area B (step 79A). Then, pattern matching is executed through comparison between pixel information of a reference image present inside the frame of the comparison area A (referred to as the reference image in the comparison area A) and pixel information of a current image present inside the frame of the comparison area B (referred to as the current image in the comparison area B) (step 79B). It is generally thought that an image is made up of a large number of pixels (see FIGS. 10(A) and 10(B)) two-dimensionally arrayed in a mesh-like pattern, and pixel information (pixel value) is stored in each of the pixels. In this embodiment, the pattern matching between the current image and the reference image is executed by utilizing those pixel values. In step 79B, the pattern matching is first executed on the pixel values (scalar quantities) of all pixels of the current image included within the frame of the comparison area B and the pixel values of all pixels of the reference image included within the frame of the comparison area A while successively moving, e.g., translating, the frame of the comparison area B in the search area 70 in each of the X- and Y-directions. More specifically, in FIG. 9(B), an upper end of the frame of the comparison area B is aligned with an upper end of the search area 70, and an upper left corner of the frame of the comparison area B is aligned with an upper left corner of the search area 70. In this state, the pixel value for each of the pixels of the reference image in the comparison area A and the pixel value for each of the pixels of the current image in the comparison area B are compared with each other while the pixels in both the images are made correspondent to each other in a one-to-one relation. This comparison is performed through steps of computing a square value of a difference between the pixel value of each pixel of the reference image in the comparison area A and the pixel value of each pixel, corresponding to the above each pixel of the reference image, of the current image in the comparison area B for all the corresponding pixels in both the comparison areas, and then adding the thus-computed square values. The total sum resulting from the above addition represents a deviation between the reference image in the comparison area A and the current image in the comparison area B set in the aforesaid position, and the aforesaid comparison represents an arithmetic operation for computing a deviation between the pixel values of all the corresponding pixels included in both the images and compared with each other. After translating the frame of the comparison area B to the right by a distance of one pixel, the above-described arithmetic operation is repeated on each pixel of the current image in the comparison area B having been translated and on each pixel, corresponding to the above each pixel of the current image, of the reference image in the comparison area A, thereby computing a deviation similar to that described above. Such a deviation is repeatedly computed for each position of the comparison area B while successively translating the frame of the comparison area B to the right (in the X-direction) on the one-pixel by one-pixel basis. When the right end of the frame of the comparison area B reaches the right end of the search area 70 with the movement of the frame of the comparison area B in the X-direction, the upper end of the frame of the comparison area B is translated by a distance of one pixel downward (in the Y-direction). Then, a similar deviation is computed in the same manner as described above for each position of the comparison area B while successively translating the frame of the comparison area B to the right (in the X-direction) on the one-pixel by one-pixel basis. Further, the movement of the frame of the comparison area B in the Y-axis is repeated. Eventually, the movement of the frame of the comparison area B is performed until the lower end and the lower right corner of the frame of the comparison area B are aligned respectively with the lower end and the lower right corner of the search area 70, whereby the above-described deviation is computed for each position of the frame of the comparison area B.

Subsequently, a primary matching area having an image similar to the reference image in the comparison area A is extracted (step 79C). More specifically, the comparison area B is extracted of which deviation has the smallest value among all of the deviations computed in step 79B through the pattern matching performed for each position of the frame of the comparison area B. Hereinafter, the extracted comparison area B will be referred to as a final comparison area B. In other words, the current image in the final comparison area B is most similar to the reference image in the comparison area A. The final comparison area B is the primary matching area. A position offset between the center (beam line m) of the current image and the center of the final comparison area B (primary matching area) is then computed (step 79D). More specifically, such a position offset is computed by using coordinate values $(X_a, Y_c)$ of the center of the current image and coordinate values $(X_{rc}, Y_{rc})$ of the center of the final comparison area B to obtain a position offset $\Delta X1$ in the X-direction between the center of the current image and the center of the final comparison area B and a position offset $\Delta Y1$ in the Y-direction between the center of the current image and the center of the final comparison area B. The position offsets $\Delta X1, \Delta Y1$ are stored in the memory provided in the positioning data generator 37.

In this embodiment, since the primary pattern matching is performed based on the reference image in the comparison area A and the current image in the comparison area B each having a restricted two-dimensional range, the time required for the pattern matching can be cut down. Particularly, the primary pattern matching is performed by linearly moving the comparison area B in the X- and Y-directions without rotating the comparison area B, and this pattern matching method also contributes to cutting down the time required for the pattern matching.

While the frame of the comparison area B is translated in the X- and Y-directions in this embodiment, it is also possible to rotate the frame of the comparison area B for the purpose of pattern matching.

As practical pattern matching methods, there are known six methods (1) to (6), given below, in addition to the one described above in the embodiment. Any of the methods (1) to (6) can be used to implement the present invention.

(1) Residual Error Matching

For the comparison area B (target pattern) and the comparison area A (master pattern), a superposition deviation (residual error) is computed from pixel information of all meshes. Then, the position of the comparison area B where the computed residual error is minimum is determined while moving the comparison area B in the up-and-down direction and the left-and-right direction.

(2) Correlation Coefficient Method

For the comparison area B (target pattern) and the comparison area A (master pattern), normalized distributions of pixel information of all meshes are separately computed. Then, the position of the comparison area B where a value of the correlation coefficient between the two computed distributions is maximum is determined while moving the comparison area B in the up-and-down direction and the left-and-right direction. This method requires a longer computing time than the residual error matching of above (1), but practical processing can be performed with speed-up through division of the distribution into layers.

(3) Phase-Only Correlation

For the comparison area B (target pattern) and the comparison area A (master pattern), pixel information patterns of all meshes are separately subjected to Fourier transformation. Then, phase-only processing is performed on the Fourier transformation plane to determine a matching point between both the patterns.

(4) Geometry Matching

This is a recently proposed matching method utilizing a series of edge points. This method enables the matching to be performed without being affected by rotation and resizing of the comparison area A (master pattern).

(5) Vector Correlation

Similarly to the geometry matching of above (4), this is a matching method utilizing a series of edge points. This method enables the matching to be performed without being affected by overlapping and hiding.

(6) Generalized Hough Transformation

This is a method obtained by extending and generalizing Hough transformation for detection of a straight line, and is primarily applied to geometrical figures. This matching method utilizes a series of edge points similarly to the above methods (4) and (5), and enables the matching to be performed without being affected by rotation and resizing, as well as by overlapping and hiding.

Note that, instead of the above methods (1) to (6), any other suitable one, e.g., the least square method used in step 81 described later, may also be used to perform the primary pattern matching.

Figure 9C:
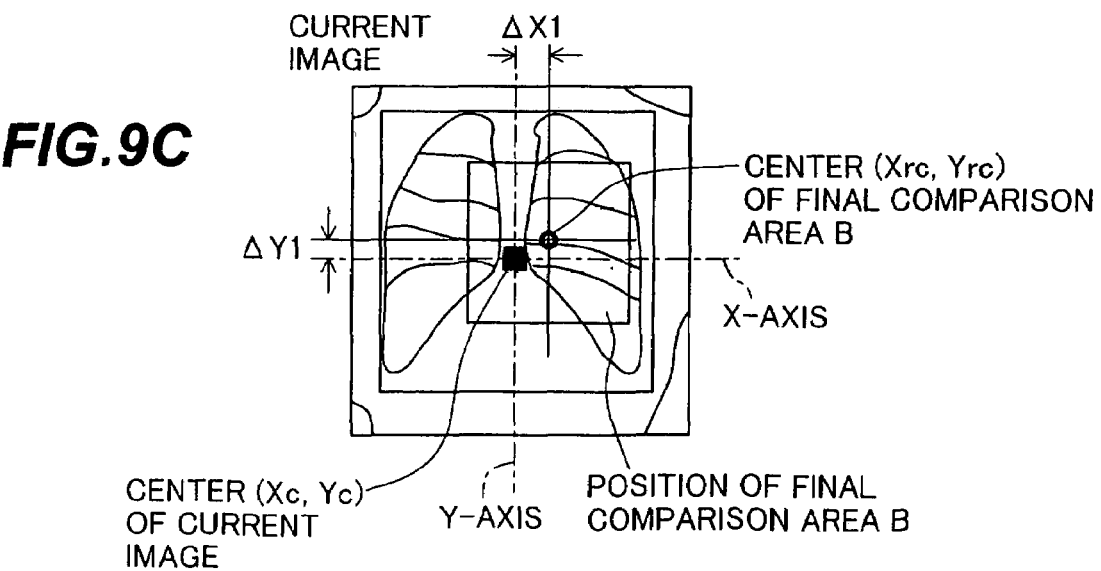

The data of the frame of the final comparison area B extracted through the primary pattern matching is outputted to the display unit 39B (step 80). With this step, the frame of the final comparison area B is displayed on the display unit 39B together with the information of the current image (see FIG. 9C).

Secondary pattern matching for the current image in the final comparison area B is executed by employing just the reference image in the comparison area A and the current image in the final comparison area B (step 81). In other words, the entire regions of the reference image and the current image are not used here. In the secondary pattern matching, the primary matching area (final comparison area B) obtained through the primary pattern matching is employed as a secondary matching candidate area. Then, based on the reference image in the comparison area A and the current image in the secondary matching candidate area (final comparison area B), the positioning data generator 37 executes coordinate transformation of the current image in the final comparison area B and finely determines the amounts of translation in the X- and Y-directions and the amount of a rotational angle at which both the images are most matched with each other. Practically, the secondary pattern matching is performed in this embodiment by using the least square method.

Figure 12:
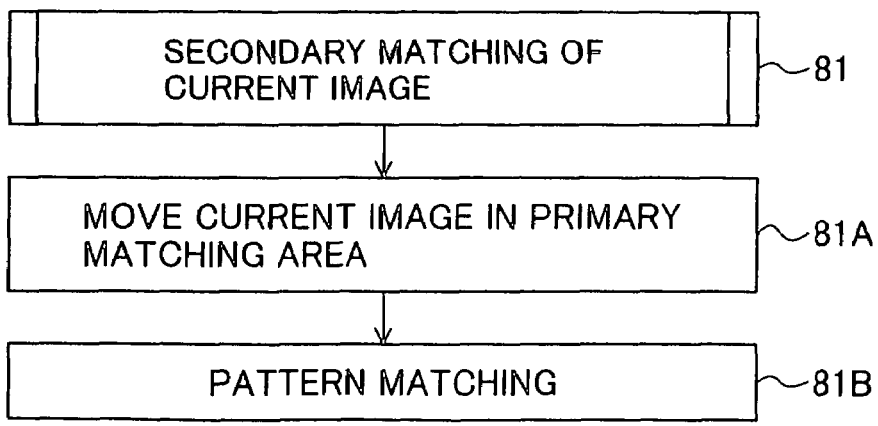
FIG. 12 is a flowchart showing a detailed processing sequence of step 81 shown in FIG. 8.

Detailed processing of step 81 will be described below with reference to FIG. 12. First, a similar area, i.e., the current image in the comparison area B, is moved and rotated (step 81A). In practice, the current image in the comparison area B is subjected to coordinate transformation by using coordinate transformation coefficients. The amount of translation and the amount of a rotational angle can be designated as the coordinate transformation coefficients. Stated another way, the movement of the comparison area B is performed by translating the current image in the final comparison area B in the X- and Y-directions and rotating it until the center of the final comparison area B (i.e., the position at which two diagonals of the final comparison area B cross each other) (see FIG. 9(C)) is aligned with the center of the current image (i.e., the beam line m) (see FIG. 10(B)). Then, pattern matching is executed (step 81B). In this pattern matching, the least square method is employed to evaluate similarity (degree of matching) between the reference image in the comparison area A the current image in the final comparison area B. More specifically, in a state of FIG. 10(B), the current image in the final comparison area B is translated in the X- and Y-directions and rotated in step 81A with respect to the reference image in the comparison area A, and the degree of matching between the moved current image in the final comparison area B and the reference image in the comparison area A is evaluated. In this embodiment, since the pattern matching is made on the reference image in the comparison area A and the current image in the comparison area B (final comparison area B) each having a restricted two-dimensional range, processing for the pattern matching can be executed in a non-wasteful manner and hence the processing time required for the pattern matching can be cut down. The processing for the pattern matching in step 81A will be described below. It is here assumed that the position of a pixel of the reference image in the comparison area A is A(X, Y) and the position of a pixel, corresponding to the above pixel of the reference image, of the current image in the final comparison area B is B(X', Y'). Thus, the position of each pixel is expressed, by way of example, as follows. The position of a pixel locating at an upper left corner of the reference image in the comparison area A is expressed by coordinate values of A(1, 1), and the position of a pixel locating at an upper left corner of the current image in the final comparison area B is expressed by coordinate values of B(1, 1). Because (X, Y) and (X', Y') representing pixels are given as coordinate information, the pixels of the reference image in the comparison area A can be made respectively correspondent to the pixels of the current image in the final comparison area B by using a coordinate transformation formula, such as an Affine transformation formula, and the current image in the final comparison area B can be translated in the X- and Y-directions and rotated in accordance with the coordinate transformation formula. A description is now made of step 81B. A square value of a difference (deviation) between the pixel value of each pixel A(X, Y) and the pixel value of each corresponding pixel B(X', Y') is computed for each pair of all the corresponding pixels in both the reference image in the comparison area A and the current image in the final comparison area B, and the thus-computed square values are added to determine the total sum. Then, while repeating the processing sequence of step 81A, i.e., translating the current image in the final comparison area B in the X- and Y-directions and rotating it with respect to the reference image in the comparison area A, the above-mentioned total sum is successively computed in step 81B. After repeating above two steps 81A and 81B, the coordinate transformation coefficients providing the minimum total sum are obtained. The thus-obtained coordinate transformation coefficients represent a position offset of the final position of the current image in the final comparison area B with respect to the reference image in the comparison area A, i.e., a position offset $\Delta X2$ in the X-direction, a position offset $\Delta Y2$ in the Y-direction, and a rotation amount (angle) $\Delta\theta$. The position offsets $\Delta X2$, $\Delta Y2$ and the rotation amount $\Delta\theta$ are all stored in the memory provided in the positioning data generator 37.

Thus, in the secondary pattern matching, the pattern matching is performed on the current image in the comparison area B having a restricted two-dimensional range and the reference image in the comparison area A also having a restricted two-dimensional range while translating the current image in the primary matching area (final comparison area B) in the X- and Y-directions and rotating it. Hence, the time required for the pattern matching can be cut down even with the matching process including the image rotation.

Note that the method used for executing the secondary pattern matching is not limited to the least square method described above, and the secondary pattern matching may be performed by using any other suitable method, for example, by executing one of the above-mentioned methods (1) to (6) again.

The data of the current image in the final comparison area B, which is located in the final position of the current image determined through the secondary pattern matching, is outputted to the display unit 39A (step 82). The current image in that final position is displayed (though not shown) on the display unit 39A in a superposed relation to the reference image in the comparison area A. By displaying the current image in that final position and the reference image on the display unit in a superposed relation to each other as described above, the operator, such as the doctor, can visually confirm the aligned state of the tumor. Then, couch (patient) positioning data is produced (step 83). Couch movement amounts (couch movement information) constituting the couch positioning data are computed by using the position offsets $\Delta X1$, $\Delta Y1$, $\Delta X2$ and $\Delta Y2$ and the rotation amount $\Delta\theta$ which are all stored in the memory provided in the positioning data generator 37. More specifically, a couch movement amount $\Delta X$ in the X-direction is computed as $(\Delta X1+\Delta X2)$, a couch movement amount $\Delta Y$ in the Y-direction is computed as $(\Delta Y1+\Delta Y2)$, and a couch movement amount (couch rotation amount) $\Delta\Theta$ in the rotating direction is computed as $\Delta\theta$. These couch movement amounts $\Delta X$, $\Delta Y$ and $\Delta\Theta$ constitute couch positioning information used for the positioning of the couch. This couch positioning information serves also as the couch movement information. Subsequently, in step 83, the couch movement amounts $\Delta X$, $\Delta Y$ and $\Delta\theta$ are outputted to and displayed on the display unit 39A.

By looking at the displayed couch movement amounts $\Delta X$, $\Delta Y$ and $\Delta\Theta$, the doctor determines whether the treatment couch 59 is to be moved to execute again for alignment of the tumor. If the doctor determines that the operation for alignment of the treatment couch is required with the movement of the treatment couch 59, the doctor inputs information indicative of "necessity of couch movement" to the positioning data generator 37 by using the input unit (not shown), the input information being separated into data per X-direction, Y-direction and rotating direction. On the other hand, if the doctor determines that the operation for aligning the tumor is not required with the movement of the treatment couch 59, the doctor inputs information indicative of "non-necessity of couch movement" to the positioning data generator 37 by using the input unit.

The positioning data generator 37 determines whether the "couch is to be moved" (step 84). More specifically, if the information inputted from the input unit indicates "non-necessity of couch movement", this means that the tumor is positioned on the beam line m. Hence, the movement of the treatment couch 59, i.e., the alignment of the tumor in the body of the patient 8 with the beam line m, is not performed by the couch driver 12, and the couch positioning process is completed. On the other hand, if the information inputted from the input unit indicates "necessity of couch movement", the couch positioning information is outputted to the couch controller 38 (step 85). Practically, the couch movement amounts $\Delta X$, $\Delta Y$ and $\Delta\Theta$ obtained in above step 83 are sent to the couch controller 38. The couch movement amounts $\Delta X$, $\Delta Y$ and $\Delta\Theta$ constitute information used for the positioning of the treatment couch 59. Thereafter, the alignment of the tumor is performed through the movement of the treatment couch 59 as described later.

While whether to move the treatment couch 59 or not is determined by the doctor in this embodiment, such a determination may be made by the positioning data generator 37. In other words, it is also possible to determine in step 84 as to "whether the couch movement amount is equal to a preset movement value (e.g., a movement value 0)" instead of "whether the couch is to be moved", and to instruct the positioning data generator 37 to carry out the movement of the couch. In this modification, more specifically, if the couch movement amounts $\Delta X$, $\Delta Y$ and $\Delta\Theta$ obtained in step 83 are each equal to the preset movement value, e.g., the movement value 0 (namely, in the case of "YES" in the determination of modified step 84), this means that the tumor is positioned on the beam line m. Hence, the movement of the treatment couch 59, i.e., the alignment of the tumor in the body of the patient 8 with the beam line m, is not performed by the couch driver 12, and the couch positioning process is completed. On the other hand, in the case of "NO" in the determination of modified step 84 (namely, if the couch movement amounts $\Delta X$, $\Delta Y$ and $\Delta\Theta$ are each not equal to the preset movement value, e.g., the movement value 0), the processing of step 85 is performed and the couch positioning information is outputted to the couch controller 38. Thus, the couch movement amounts $\Delta X$, $\Delta Y$ and $\Delta\Theta$ obtained in step 83 are sent to the couch controller 38. Additionally, in modified step 84, information indicating the determination result, i.e., "completion of the patient positioning" or "re-execution of the patient positioning" is outputted to and displayed on, for example, the display unit 39A. In the case of "re-execution of the patient positioning", the couch movement amounts $\Delta X$, $\Delta Y$ and $\Delta\Theta$ are outputted to and displayed on the display unit 39A.

The couch controller 38 receives respective detected data regarding X- and Y-directional positions (X0, Y0) of the treatment couch 59 and a rotational angle (e.g., $\Theta0$) thereof in the rotating direction in the state before the X-ray is irradiated from the X-ray emission device 26 as described above. Those data are detected by respective sensors (not shown) disposed on the couch driver 12. Also, the couch controller 38 receives the couch movement amounts $\Delta X$, $\Delta Y$ and $\Delta\Theta$ and compute the position of the treatment couch 59, i.e., $(X0+\Delta X)$, $(Y0+\Delta Y)$ and $(\Theta0+\Delta\Theta)$, to which it is to be moved. Then, the couch controller 38 drives the motors 11a, 11c and 11d to move the treatment couch 59 so that the position of the tumor in the body of the patient 8 lying on the treatment couch 59 is aligned with the computed position.

After moving the treatment couch 59 in such a manner, the X-ray irradiation along the beam line m is performed on the patient 8 again, and the processing of steps 72 to 84 are repeated by the positioning data generator 37 using the current image captured by the X-ray image capturing device 29 until the information "non-necessity of couch movement" is inputted in step 84.

With the patient positioning device of this embodiment, as described above, pattern matching is performed on the reference image in the set comparison area A and the current image in the set comparison area B to produce information for the positioning of the patient (couch). In the prior-art case of requiring the operator to set particular monuments, landmarks, anatomical base points, or the likes to produce patient positioning data based on them, the positions of the monuments or the likes must be designated on each of the reference image and the current image at high accuracy without an offset between the reference image and the current image. However, it is difficult, as mentioned before, to designate corresponding positions on the reference image and the current image without an offset between them. With this embodiment, since the reference image in the set comparison area A and the current image in the set comparison area B are subjected to the pattern matching, the operator is not required to designate the positions of the monuments or the likes, and hence the accuracy in producing the patient positioning data is avoided from being affected by the skills of individual operators. Accordingly, the patient positioning accuracy can be increased regardless of the skills of individual operators. As a result, a patient positioning device can be constructed of which operation does not depend upon amounts of the skills of individual operators. Further, it is possible to cut the time and labor required for setting the monuments or the likes, and to quickly and smoothly carry out the positioning operation.

With this embodiment, since the movement amount of the treatment couch 59 (specifically the movement amount of the tumor in the body of the patient 8 lying on the treatment couch 59) is determined through pattern matching made on a plurality of corresponding areas (e.g., pixels) in both the above-mentioned images, the positioning accuracy of the treatment couch 59 with respect to the beam line m is further increased. In addition, with this embodiment, since the pattern matching between the reference image and the current image is performed by using respective image information (pixel values of respective pixels) specific to the reference image and the current image, there is no need of adding new information for the pattern matching.

Figure 13:
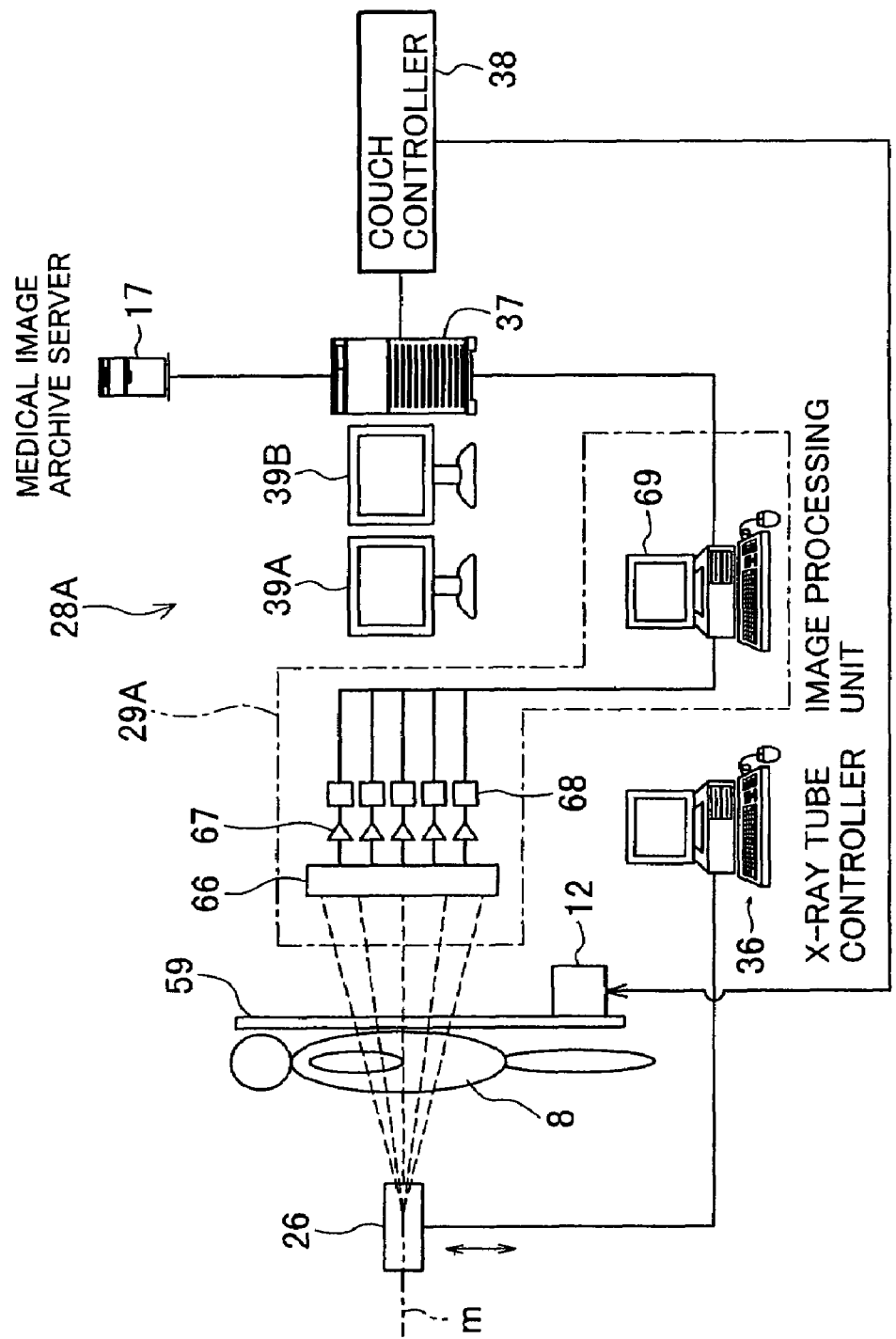
FIG. 13 is a schematic view showing a construction of a modification of the patient positioning device according to the one preferred embodiment of the present invention.

While the above embodiment has been described as using the X-ray image capturing device 29 including the X-ray fluorescence multiplier 30, an X-ray image capturing device (image information generator) 29A may be used instead of the X-ray image capturing device 29 shown in FIG. 13.

A patient positioning device 28A using the X-ray image capturing device 29A, according to another embodiment of the present invention, will be described below with reference to FIG. 13. The patient positioning device 28A differs from the above-described patient positioning device 28 in using the X-ray image capturing device 29A. More specifically, the X-ray image capturing device 29A comprises a plurality of semiconductor radiation detectors (X-ray entry devices or flat panel detector) 66, a plurality of signal amplifiers 67, a plurality of signal processors 68, and an image processing unit (image information producing unit) 69. Looking from the direction along the beam line m, the plurality of semiconductor radiation detectors 66 are arranged in a grid pattern comprising a plurality of rows in the X-direction and a plurality of columns in the Y-direction, which are arrayed in a closely contacted state with each other. The signal amplifiers 67 and the signal processors 68 are disposed in a one-to-one relation to the semiconductor radiation detectors 66 and are serially connected to corresponding ones of the semiconductor radiation detectors 66. Information outputted from the individual signal processors 68 and indicating the intensity of X-ray is sent to the image processing unit 69.

An X-ray beam for detecting the tumor in the body of the patient 8 is emitted from the X-ray emission device 26, which has been moved to position on the beam line m, and penetrates the tumor and the surroundings thereof. Then, the X-ray beam enters the flat panel detector (all the semiconductor radiation detectors 66) disposed on the side of the treatment couch 59 away from the patient 8 for conversion into electrical signals. The electrical signal outputted from each of the semiconductor radiation detectors 66 is amplified by the corresponding signal amplifier 67 and is integrated by the corresponding signal processor 68 for a preset interval of time. As a result of integrating the electrical signal, X-ray intensity information is obtained. The image processing unit 69 produces image information (information of a current image or a captured image) by using the X-ray intensity information outputted from each signal processor 68. The information of the current image is taken into the positioning data generator 37, which executes similar processing to that described in the above embodiment.

This modified embodiment can also provide similar advantages as those obtained with the above embodiment.

According to the present invention, as will be seen from the above description, a sufficient level of patient positioning accuracy can always be ensured regardless of the skills of individual operators.

What is claimed is:

1. A patient positioning device for positioning a couch supporting a patient to which a charged particle beam is irradiated from a particle beam irradiation system, said patient positioning device comprising:

an X-ray emission device;

an image information generator for generating second image information regarding a portion of the patient lying across the path of said charged particle beam by using a signal depending on the X-ray emitted from said X-ray emission device; and a processing unit for setting, with respect to a first image information which serves as a reference image prepared beforehand based on image data of a tumor in the body of the patient and including an isocenter, a first set area smaller than an area of said first image information and including said isocenter, setting, with respect to the second image information, a second set area smaller than an area of said second image information and having substantially the same size as said first set area and including a position corresponding to the path of said charged particle beam, executing primary pattern matching between the first image information in said first set area and the second image information in said second set area by moving said second set area within said area of said second image information to determine a primary matching area having said second image information most similar to said first image information in said first set area, and executing secondary pattern matching comparing the first image information in said first set area and the second image information in said primary matching area by moving the second image information in said primary matching area relative to the first image information in said first set area, thereby producing information used for positioning of said couch based on a positional offset between said second image information in said second set area before executing said primary pattern matching and said second image information in said primary matching area determined by said primary pattern matching and a positional offset between said second image information in said primary matching area determined by said primary pattern matching and said second image information in said primary matching area provided by said secondary pattern matching.

2. A patient positioning device according to claim 1, wherein said image information generator comprises an X-ray transducer for converting the incident X-ray into light, and a camera for capturing the light and producing the second image information.

3. A patient positioning device according to claim 1, wherein said image information generator comprises a plurality of semiconductor radiation detectors for converting the incident X-ray into electrical signals, a plurality of signal processors disposed in a one-to-one relation to said semiconductor radiation detectors and processing said electrical signals, and an image information producing unit for receiving outputs from said signal processors and producing the second image information.

4. A patient positioning device according to claim 1, further comprising a couch controller for controlling movement of said couch in accordance with said positioning information.

5. A patient positioning device according to claim 1, wherein said processing unit executes the pattern matching by using information of a plurality of pixels contained in the first image information in said first set area and information of a plurality of pixels contained in the second image information in said second set area.

6. A patient positioning device according to claim 5, wherein said processing unit produces said positioning information based on the least square method such that a deviation between the information of a plurality of pixels contained in the first image information in said first set area and the information of a plurality of pixels contained in the second image information in said second set area is minimized.

7. A patient positioning device according to claim 1, further comprising a display unit for displaying the first image information and the second image information, wherein said processing unit displays said frame showing said first set area and said frame showing said second set area on said display unit.

8. A patient positioning device according to claim 1, wherein said display unit comprises a first display unit for displaying the first image information and a second display unit for displaying the second image information, said second display unit being separate from said first display unit.

9. A patient positioning device according to claim 1, wherein said X-ray emission device is mounted to said particle beam irradiation system and movable between a first position located in a path of said charged particle beam and a second position located away from the path of said charged particle beam to be out of interference with advance of said charged particle beam, and configured to emit an X-ray in said first position.

10. A patient positioning device according to claim 1, wherein said processing unit evaluates the degree of matching between the first image information in said first set area and the second image information in said primary matching area when comparing them in said secondary pattern matching.

11. A patient positioning method for positioning a couch supporting a patient to which a charged particle beam is irradiated from a particle beam irradiation system, said patient positioning method comprising the steps of:

generating, based on the X-ray having penetrated a portion of the patient lying across the path of said charged particle beam, second image information regarding the portion of the patient;

setting, with respect to a first image information which serves as a reference image prepared beforehand based on image data of the tumor in the body of the patient and including an isocenter, a first set area smaller than an area of said first image information and including said isocenter;

setting, with respect to the second image information, a second set area smaller than an area of said second image information and having substantially the same size as said first set area and including a position corresponding to the path of said charged particle beam;

executing primary pattern matching between the first image information in said first set area and the second image information in said second set area by moving said second set area within said area of said second image information to determine a primary matching area having said second image information most similar to said first image information in said first set area; and executing secondary pattern matching comparing the first image information in said first set area and the second image information in said primary matching area by moving the second image information in said primary matching area relative to the first image information in said first set area, thereby producing information used for positioning of said couch based on a positional offset between said second image information in said second set area before executing said primary pattern matching and said second image information in said primary matching area determined by said primary pattern matching and a positional offset between said second image information in said primary matching area determined by said primary pattern matching and said second image information in said primary matching area provided by said secondary pattern matching.

12. A patent positioning method according to claim 11, wherein said secondary pattern matching is executed by evaluating the degree of matching between the first image information in said first set area and the second image information in said primary matching area when comparing them.

* * * * *